United States Patent
Craelius et al.

(10) Patent No.: US 9,877,682 B2
(45) Date of Patent: Jan. 30, 2018

(54) GESTURE RECOGNITION BIOFEEDBACK

(71) Applicant: Rutgers, The State University of New Jersey, New Brunswick, NJ (US)

(72) Inventors: William Craelius, Piscataway, NJ (US); Don Yungher, New Brunswick, NJ (US); Nam H. Kim, Paramus, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/928,280

(22) Filed: Oct. 30, 2015

(65) Prior Publication Data

US 2016/0051183 A1 Feb. 25, 2016

Related U.S. Application Data

(63) Continuation of application No. 13/407,353, filed on Feb. 28, 2012, now Pat. No. 9,173,612.

(60) Provisional application No. 61/447,466, filed on Feb. 28, 2011, provisional application No. 61/447,980, filed on Mar. 1, 2011.

(51) Int. Cl.
*A61B 5/00* (2006.01)
*A61B 5/11* (2006.01)

(52) U.S. Cl.
CPC ............ *A61B 5/486* (2013.01); *A61B 5/1107* (2013.01); *A61B 5/1125* (2013.01); *A61B 5/6824* (2013.01); *A61B 5/6843* (2013.01); *A61B 5/1124* (2013.01); *A61B 2505/09* (2013.01); *A61B 2562/043* (2013.01)

(58) Field of Classification Search
CPC ....... A61B 5/11; A61B 5/1107; A61B 5/1124; A61B 5/1125; A61B 5/486; A61B 5/6824; A61B 5/6843; A61B 2505/09
See application file for complete search history.

(56) References Cited

U.S. PATENT DOCUMENTS

| | | | |
|---|---|---|---|
| 6,516,289 B2* | 2/2003 | David | A61B 5/4041 128/903 |
| 8,187,209 B1 | 5/2012 | Giuffrida | |
| 8,435,177 B2* | 5/2013 | Lanfermann | A63B 24/0006 434/247 |
| 8,821,416 B2 | 9/2014 | Johnsson et al. | |
| 8,827,930 B2 | 9/2014 | Wekell | |
| 8,830,162 B2 | 9/2014 | Helmer | |

(Continued)

OTHER PUBLICATIONS

Steenbergenet al, "Fingertip force control during bimanual object lifting in hemiplegic cerebral palsy" Experimental Brain Research. 2008;186(2):191-201.

(Continued)

*Primary Examiner* — Max Hindenburg
(74) *Attorney, Agent, or Firm* — Stephen H. Eland; Dann, Dorfman, Herrell & Skillman

(57) ABSTRACT

A gesture recognition biofeedback device is provided for improving fine motor function in persons with brain injury. The system detects a physical characteristic of the patient and provides feedback based on the detected characteristic. For instance, the system may detect surface muscle pressures of the forearm to provide real-time visual biofeedback to the patient based on a comparison of the detected muscle pressure and predefined values indicative of appropriate motor function.

7 Claims, 2 Drawing Sheets

(56) References Cited

U.S. PATENT DOCUMENTS

| | | |
|---|---|---|
| 8,845,494 B2 | 9/2014 | Whitall et al. |
| 8,845,556 B1 | 9/2014 | Schickler et al. |
| 8,852,129 B2 * | 10/2014 | Lee .................. A61B 5/1101 600/595 |
| 9,173,612 B2 * | 11/2015 | Craelius ............ A61B 5/1107 |

OTHER PUBLICATIONS

Armagan et al, "Electromyographic biofeedback in the treatment of the hemiplegic hand: a placebo-controlled study" Am. J. Phys. Med. Rehabil. 2003;82:856-61.

K.S. Turker, "Electromyography: Some Methodological Problems and Issues" Physical Therapy. 1993;73(10), 698-710.

Wininger et al, "Pressure Signature of Forearm as Predictor of Grip Force" J. Rehab. Res. Dev. 2008;4(6):883-892.

Phillips et al, "Residual Kinetic Imaging: A Versatile Interface for Prosthetic Control" Robotica. 2005;23:277-82.

Grice et al, "Adult norms for a commercially available Nine Hole Peg Test for finger dexterity" Am. J. Occ. Ther. 2003; 57:570-3.

Hesse et al, "Ankle Muscle Activity Before and After Botulinum Toxin Therapy for Lower Limb Extensor Spasticity in Chronic Hemiparetic Patients" Stroke. vol. 27, pp. 455-460, 1996.

Teixeira-Salmela et al, "Muscle Strengthening and Physical Conditioning to Reduce Impairment and Disability in Chronic Stroke Survivors" Arch. Phys. Med. Rehabil. 1999;80:1211-1218.

Volpe et al, "A novel approach to stroke rehabilitation: Robot-aided sensorimotor stimulation" Neurology. 2000;54 (10):1938-1944.

Prochazka et al, "Positive Force Feedback Control of Muscles" J. Neurophys. 1997;77(6):3226-36.

Alon et al, "Functional Electrical Stimulation Enhancement of Upper Extremity Functional Recovery During Stroke Rehabilitation: A Pilot Study" Neurorehabilitation and Neural Repair. 2007;21(3):207-15.

Fasoli et al, "Robotic Technology and Stroke Rehabilitation: Translating Research into Practice" Topics in Stroke Rehab. 2004;11(4):11-19.

* cited by examiner

**INDICATES STATISTICAL SIGNIFICANCE (p<0.05)

GESTURE RECOGNITION BIOFEEDBACK

This application is a continuation of U.S. patent application Ser. No. 13/407,353 filed Feb. 28, 2012. This application also claims priority to U.S. Provisional Patent Application Nos. 61/447,466 filed on Feb. 28, 2011 and 61/447,980 filed on Mar. 1, 2011. The entire disclosure of each of the foregoing applications is incorporated herein by reference.

FIELD OF THE INVENTION

The present invention relates to the field of providing therapy for individuals suffering a brain injury. In particular, the present invention is directed to a system for providing biofeedback to a patient during a therapeutic activity to improve the effectiveness of the therapy.

BACKGROUND

Grasping is fundamental to activities of daily living (ADL) and is usually impaired following stroke and traumatic brain injury. In the absence of grasping, the impaired arm tends to be neglected, retarding its recovery; accordingly, grasp training is a high priority for rehabilitation of the upper limb.

Repetitive training tasks are often difficult for brain injured individuals, due not only to their motor deficits, but also to their tactile and proprioceptive deficits. Although there are reports in the literature of inconclusive evidence, many studies many studies have documented the efficacy of EMG biofeedback. For example, a group of hemiplegic patients who were given occupational therapy plus EMG-biofeedback improved their upper limb function relative to a control group receiving only occupational therapy]. Biofeedback from the EMGs of the extensor carpi radialis and extensor digitorum communis improved the wrist and finger extension of stroke subjects. EMG biofeedback has even been proposed as a therapy for remotely supervising home users. The method, however, remains a challenge, as EMG requires expertise and is difficult for self-application and interpretation. A more fundamental problem of using EMG for biofeedback is that electrical activities of muscle vary considerably from one repetition to the next, even when the underlying movement is kinematically consistent.

DETAILED DESCRIPTION

Figure 1:
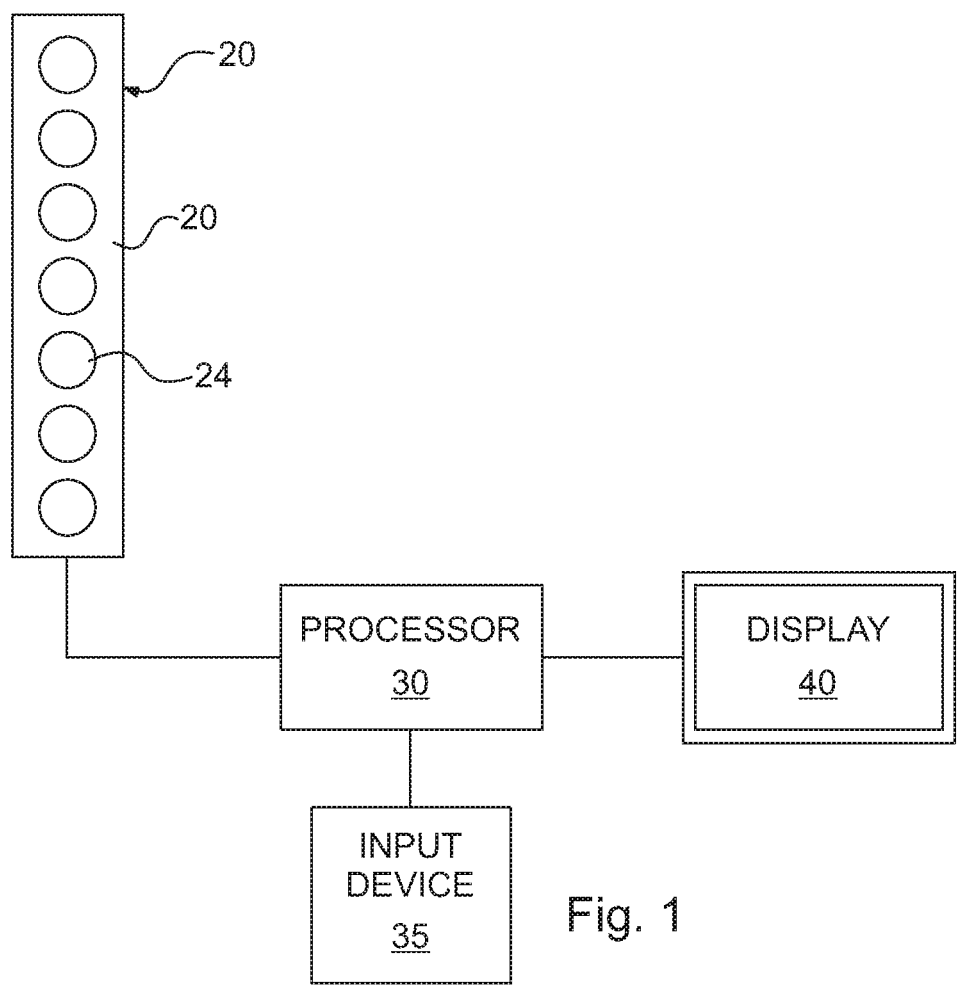
FIG. 1 is a schema of a Gesture Recognition Biofeedback recording system.

Referring now to the Figures In general and to FIG. 1 specifically, a system for providing gesture recognition biofeedback (GRB) for improving fine motor function in individuals who have a brain injury is designated generally 10. The system uses visual feedback to relay the accuracy of specific gestures and uses a simpler interface than systems relying upon specific muscular activation amplitudes.

The system 10 includes a sensing device 20 for sensing muscular operation of a subject. The sensing device 20 provides electrical signals to a processor 30, which processes the signals received from the sensing device. Based on the signals received from the sensing device, the processor provides visual feedback on a display, such as a video display 30.

The sensing device 20 may be designed to be readily attachable to a patient. For instance, in the present instance, the sensing device includes a cuff 22 that can be placed around the forearm of the patient. The cuff 22 may be adjustable, such as by an elastic band or a fastener, such as a hook and loop fastener. The sensing device 20 includes one or more sensors or detectors 24 for detecting a physical characteristic. In the present instance, the sensing device includes seven sensors 24 for detecting muscle contraction. Specifically, the sensors 24 are force sensors for detecting force applied against the sensor when the sensor is against or adjacent the skin of the patient.

The processor 30 may be any of a variety of processors, such as the microprocessor of a personal computer. The processor may be electrically connected with the sensing device by a wired connection, such as a cable. Alternatively, the sensing device 20 may include a wireless transmitter for wirelessly transmitting the signals from the sensors. The processor 30 may be connected with a wireless receiver for receiving wireless signals from the sensing device 20.

The processor 30 processes the signals from the sensing device to determine whether the signals indicate a desired type of movement. The desired type of movement may by a specific movement from the patient or a specific amount of movement or both. In the present instance, the processor monitors the signals from the sensing device 20 to detect whether the signals indicate an appropriate grasping motion by the patient. Specifically, the processor 30 compares the signals received from the sensing device during a therapy session and compares the signals against predetermined values. Based on the comparison, the processor 30 determines whether the signal indicates the desired grasping motion.

The processor 30 provides signals to an output mechanism for providing feedback to the patient. The output mechanism may be any of a variety of devices providing visual, auditory or tactile feedback to the patient. For instance, the output mechanism can be a speaker to provide an audial cue to the patient that the patient can hear to determine whether or not the patient made the desired movement, such as a grasping motion sufficient to grasp an item. Similarly, the output mechanism may provide tactile feedback, such as a motor for providing a vibration. In the present instance, the output mechanism is a display, such as a video screen. The display provides a graphical image to signal the patient if the patient made the desired movement.

The system may also include an output mechanism for prompting the patient in addition to the output mechanism for the biofeedback discussed above. As with the biofeedback element discussed above, the output mechanism can be used to provide a visual, audial and/or tactile signal to the user. For instance, the system 10 may include an audio device for providing audial cues to the patient, which may be used to prompt the patient to perform a particular task. Alternatively, the biofeedback mechanism can also be used to provide to prompt the patient. For instance, the display 40 may include a signal to perform a particular task along with an image providing biofeedback about the patient's performance of the task.

In the present instance, the sensing element 20 uses Surface Muscle Pressure (SMP) to record muscle activation during fine motor tasks. SMP registers voluntary effort during grasping with the sensorized cuff worn on the forearm. Gesture recognition feedback operates by displaying the difference between SMP sensor outputs and a pre-recorded gesture template defined as directed by a clinician providing the user with guidance in repetitive task performance that can be remotely monitored.

EXAMPLE

Participants

The system 10 was used with an experimental group comprising both stroke (n=4) and TBI (n=8) subjects, 8 male and 4 female. Ten of the subjects were right-hand dominant. Their mean age was 39.8 years, with a range of 21 to 69 years. All had mild to moderate spasticity, as assessed by an Occupational Therapist, and could complete the 9-Hole Peg Test (HPT). In addition to the experimental group, seven healthy subjects participated as a cohort of control subjects, approximately age-matched to the experimental group, with a mean age of 46.4 years ranging from 25 to 67 years. None reported any neurological or biomechanical impairment in either upper extremity.

Biofeedback

The sensing device 20 monitored surface muscle pressure (SMP). The SMP was recorded with a sensorized therapeutic cuff placed comfortably around the forearm. The sensing device included seven 0.5" diameter force sensing resistors made by Interlink Electronics. The sensors 24 were moveable within the cuff 22 so that the sensors could be evenly spaced around each subject's forearm. While the sensors were distributed uniformly, they were not targeted to specific locations on the arm. Signals from the sensing device 20 were acquired at a sampling rate of 25 Hz. The cuff was applied around the forearm with a comfortable static pressure, providing a positive baseline that allowed detection of local pressure changes in the limb.

Biofeedback was generated as a comparison between real-time SMP values and those previously recorded as a template for desirable activity. To set the template, subjects were instructed to continue resting while the "relax" state was captured. Subjects were then instructed to "pinch", producing a thumb-index opposition, with attention to the posture of the hand. SMP values from the final 200 ms of capture were averaged to generate a template value for each sensor.

For training, subjects were given auditory cues to pinch and relax, alternately presented every 4 seconds. Biofeedback was generated as a scalar value, which was derived from the multi-dimensional information from all seven SMP sensors. The pinch template was defined as a static point in sensor space whose location was defined during template setting. The real-time SMP values defined a point in the sensor space representative of forearm muscle activity.

During set-up, a clinician can monitor the movement of the patient as the patient performs a desired task, such as pinching. While guiding and/or monitoring the patient during the task, the sensing device can monitor the patient's movement by providing SMP values to a processor. Since the clinician is observing the patient, the clinician can ensure that the patient's movement was acceptable. The processor can then analyze the SMP values to determine a template of predetermined SMP values for each of the sensors corresponding to an acceptable movement by the particular patient.

In the present instance, to resolve the real-time and template SMP values into information about performance, their locations were compared using the Euclidean distance, a simple spatial metric that decreased as the real-time SMP approached the template in sensor space, calculated as $$GRB = 10 - \sqrt{\sum_{i=1-7}(Target\text{-}i - SMP\text{-}i)^2} \quad \text{Equation 1}$$

A display provided feedback by displaying an image of a tank whose fullness was determined by the GRB feedback value based on signals from the sensing device. The image provided increased visual feedback as thumb-index opposition more closely met the clinician-directed template.

Protocol

During training, subjects were instructed to pinch as in template setting. In the With Feedback (WF) condition, visual feedback was given as described above. In the No Feedback (NF) condition, the subject was instructed to either pinch or rest according to the auditory timing cues, but no visual feedback was given. Sessions included approximately 30 repetitions per condition, with two rest periods provided as necessary.

Participants were pseudo-randomly assigned to two groups, which determined the order that feedback conditions were used in training. One group (WF-NF) had biofeedback in the first training session and no feedback during the second session. The NF-WF group was trained in the opposite order. The same grouping scheme was used for the control subjects.

Fine motor function was assessed by the HPT, which was administered using standard pegs and peg board. Subjects were instructed to fill the board peg-by-peg, then to remove pegs one at a time. They were instructed to complete this test as quickly as possible and using only the affected hand. The HPT was performed three times during the study: first as a pre-training baseline, then after each of the two training conditions.

Analysis

Results from the HPT were compared within subjects as the difference between the time to completion of a test and that of the preceding instance, normalized within subjects by dividing each difference by the baseline time. To measure their independence from training order, HPT times were compared between the two training order groups. This analysis was performed both for WF training and for NF training, using the non-parametric Mann-Whitney test. Low significance from this analysis would indicate that the training order was irrelevant and the two groups could be combined.

HPT times following both NF and WF training were compared using the Wilcoxon signed-rank test, as data were collected in two conditions for each subject. In all cases, the null hypothesis of these tests was the expectation that the two experimental conditions yielded identical times on the HPT.

The inclusion criteria were additionally narrowed in further post-hoc processing. Separately analyzing a subset of participants whose baseline HPT exceeded an arbitrary minimum allowed inferences about the efficacy of the device for users with more severe impairment. The arbitrary limit used herein was 50 seconds.

Results

Figure 2:
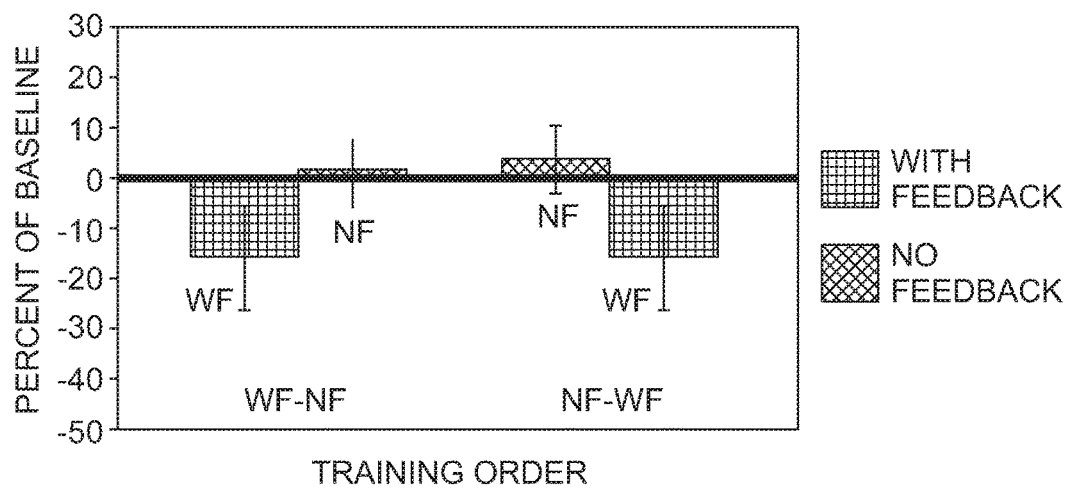
FIG. 2 is a graphical representation of training results for 12 impaired subjects, grouped equally according to training order, either WF-NF or NF-WF. Note that HPT scores (as percent of baseline, mean±S.E.) were better for the WFcondition in both groups.

For the impaired groups, the dependence of training order was analyzed, and no significant effect was found ($p > 0.7$), as seen in FIG. 2. Based on this result, the two groups were combined, and subsequent analyses were conducted independently of training order. After one session of training by all impaired subjects with feedback (WF), the average decrease in HPT time to completion was 16.1%±6.98%. In contrast, training with no feedback (NF) slightly increased the HPT time by 2.07%±3.61% (FIG. 1).

Figure 3:
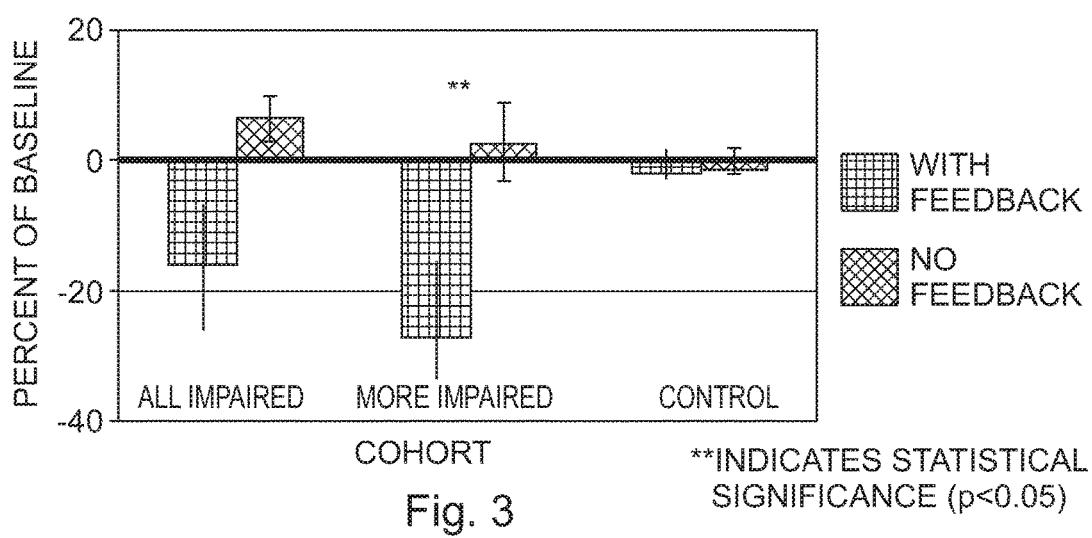
FIG. 3. Is a graphical representation of the changes in HPT scores (as percent of baseline, mean±S.E.). The left comparison represents results from all impaired subjects; the center comparison represents results from a more impaired subset of subjects; and the right comparison represent results from the control subjects.

A subset of the impaired subjects was established, using the criterion of a minimum of 50 seconds to complete the baseline HPT. This resulted in a cohort of seven subjects, treated as a single cohort regardless of training order. Results from this cohort of more severely impaired subjects were compared to the results from the entire impaired group (FIG. 3). GRB training yielded an improvement of 27.3%±9.93%. In the absence of GRB training, there was a 2.07%±3.61% decline in performance. The difference between the two was statistically significant ($p<0.05$).

GRB training negligibly affect HPT scores of the control subjects, as shown in FIG. 2. The minimal training effect was independent of training orders, and all controls were therefore combined into one cohort. Across all controls, the average HPT times after the WF and NF sessions decreased slightly by 1.31%±2.47%, and 0.74%±1.8%, respectively.

Discussion

Validity

Analyzing the efficacy of training with GRB is complicated by the range of impairments that result from brain injuries. Fine motor function was assessed using an independent rater, the HPT, a commonly used outcome for stroke rehabilitation. Since non-uniformity within the cohort of brain injured subjects was unavoidably present, statistical analyses were non-parametric, and not based on the assumption of normal distributions. The Mann Whitney and Wilcoxon signed rank tests were therefore used to test significance.

Approximately 30 repetitions of the thumb-index opposition were performed in each training condition, split evenly into three sets by resting periods of approximately one minute. This number of repetitions was sufficient to facilitate the improvement of fine motor function during training with biofeedback. However, without feedback, thirty repetitions were not likely to improve performance, even in the most impaired subjects.

It is possible that additional training time might have facilitated some improvement in the NF condition. The total number of sixty repetitions seemed to be the best compromise possible between avoiding fatigue and maximizing training time. While some studies have used more repetitions during training, as many as two hundred, some have used only thirty to sixty repetitions.

The impaired group included 8 subjects with traumatic and 4 subjects with ischemic brain injuries. Since no difference in trend was noted between the two injury types, we combined both types into a single group using a previously validated approach.

Experimental Design

Analyzing the efficacy of therapies for brain injuries due to trauma or stroke is complicated by the range of associated impairments. Here, fine motor function was assessed using an independent rater, the HPT, a commonly used outcome for stroke rehabilitation. The impaired group included eight subjects with traumatic and four subjects with ischemic brain injuries. Since no difference in trend was noted between the two injury types, we combined both types into a single group, similarly to a previous approach, and used nonparametric statistical analysis, not based on the assumption of normal distributions. In this way, subjects' changes in HPT time after WF training were compared to their own control (NF) condition.

Approximately 30 repetitions of the thumb-index opposition were performed in each training condition, split evenly into three sets by resting periods of approximately one minute. This number of repetitions was sufficient to facilitate the improvement of fine motor function during training with biofeedback. However, without feedback, thirty repetitions were not likely to improve performance even in the most impaired subjects.

It is possible that additional training time might have facilitated some improvement in the NF condition. The total number of 60 repetitions seemed to be the best compromise possible between avoiding fatigue and maximizing training time. While some studies have used more repetitions during training, as many as two hundred, some have used only 30-60 repetitions.

Although the effects of stroke and TBI are thought to be generally dissimilar, the non-parametric, paired Wilcoxon signed-rank analysis used here treats improvements within subject.

The thumb-index opposition was selected as a representative task, as a prehensile movement critical to ADL and a common task in studies of motor control. The NF condition is representative of a typical rehabilitation protocol, in which a subject repetitively performs a task without a therapeutic device. It is similar to the control condition in a number of studies comparing new rehabilitative methods to standard training. Using both NF and WF training for each subject in a cross-over experimental design allowed the use of a repeated-measures statistical analysis. The randomization of training orders accounted for the possibly confounding effects of fatigue or other changes during an experimental session. The close parallel between training effects for the WF-NF group and the NF-WF group can be seen in FIG. 2, indicating the lack of effect of training order. For this reason, the possibility of a confounding effect from fatigue, cognition, or other artifactual influences as detailed above can be dismissed as negligible.

Among the impaired subjects, there was a diversity of impairment level, as indicated by a wide range of baseline HPT time, from 28 to 263 s. Selecting a threshold of 52 s as a separation criterion resulted in a subset of seven more impaired subjects. As can be seen in FIG. 3, the more impaired group improved by 27.3% (S.D. 9.93%) with GRB which was significantly more efficacious than NF training.

Clinical Implications

The efficacy of acute training with GRB was tested in a pinching task with impaired subjects. Results from HPT testing showed that subjects decreased their time to completion of the HPT to a greater extent after training with the biofeedback than after the no-feedback condition. GRB provides real-time visual feedback during repetitive grasping tasks that yields acute improvement in a single session of training. Since SMP does not require the precise placement of sensors on specific muscles, GRB is easily donned and simple to interpret. GRB therefore offers the user a simple means for retraining fine motor function of the hand without the supervision of a clinician. These results suggest that GRB has practical advantages over traditional biofeedback and can improve motor function, related to ADL in brain-injured individuals.

REFERENCES

The following materials provide background for the foregoing description, and the entire disclosure of each of the following publications is incorporated herein by reference.

D. A. Nowak, C. Grefkes, M. Dafotakis, J. Kust, H. Karbe, and G. R. Fink. Dexterity is impaired at both hands following unilateral subcortical middle cerebral artery stroke. *European Journal of Neuroscience.* 2007; 25(10): 3173-3184.

G. Kwakkel and B. Kollen, Predicting improvement in the upper paretic limb after stroke. *Restorative Neurology and Neuroscience.* 2007; 25(5):453-460.

B. Steenbergen, J. Charles, and A. M. Gordon, Fingertip force control during bimanual object lifting in hemiplegic cerebral palsy. *Experimental Brain Research.* 2008; 186 (2):191-201.

J. M. Blennerhassett, L. M. Carey, and T. A. Matyas, Clinical measures of handgrip limitation relate to impaired pinch grip force control after stroke. *Journal of Hand Therapy.* 2008; 21(3):245-253.

N. Byl, et al Effectiveness of Sensory and Motor Rehabilitation of the Upper Limb Following the Principles of Neuroplasticity: Patients Stable Poststroke. *Neurorehab and Neural Repair.* 2003; 17:176-191.

Y. Tian, L. G. Kang, H. Y. Wang, and Z. Y. Liu, Biofeedback therapy improves motor function following stroke. *Neural Regeneration Research.* 2010; 5(7):538-544.

O. Armagan, Tascioglu F., Oner C. Electromyographic biofeedback in the treatment of the hemiplegic hand: a placebo-controlled study. *Am J Phys Med Rehabil.* 2003; 82:856-61.

K. S. Turker. Electromyography: Some Methodological Problems and Issues. *Physical Therapy.* 1993; 73(10), 698-710.

M. T. Wininger, N. H. Kim, W. Craelius. Pressure Signature of Forearm as Predictor of Grip Force. *J Rehab Res Dev.* 2008; 4(6):883-892.

S. Phillips and W. Craelius. Residual Kinetic Imaging: A Versatile Interface for Prosthetic Control. *Robotica.* 2005; 23:277-82.

K. Grice, K. A. Vogel, L. Viet, A. Mitchell, S. Muniz, M. A. Vollmer. Adult norms for a commercially available Nine Hole Peg Test for finger dexterity. *Am J Occ Ther.* 2003; 57:570-3.

P. Langhorne, R. Wagenaar, and C. Partridge. Physiotherapy after stroke: more is better? *Physiotherapy Research International.* 1996; 1(2):75-88.

S. Hesse, et al. Ankle Muscle Activity Before and After Botulinum Toxin Therapy for Lower Limb Extensor Spasticity in Chronic Hemiparetic Patients. *Stroke.* vol. 27, pp. 455-460, 1996.

L. F. Teixeira-Salmela, S. J. Olney, S. Nadeau, and B. Brouwer. Muscle Strengthening and Physical Conditioning to Reduce Impairment and Disability in Chronic Stroke Survivors. *Arch Phys Med Rehabil.* 1999; 80:1211-1218.

B. T. Volpe, et al. A novel approach to stroke rehabilitation: Robot-aided sensorimotor stimulation. *Neurology.* 2000; 54(10):1938-1944.

A. Prochazka, D. Gillard, and D. J. Bennett. Positive Force Feedback Control of Muscles. *J Neurophys.* 1997; 77(6): 3226-36.

G. Alon, A. F. Levitt, P. A. McCarthy. Functional Electrical Stimulation Enhancement of Upper Extremity Functional Recovery During Stroke Rehabilitation: A Pilot Study. *Neurorehabilitation and Neural Repair.* 2007; 21(3):207-15.

R. K. Bode and A. W. Heinemann. Course of functional improvement after stroke, spinal cord injury, and traumatic brain injury. *Arch Phys Med and Rehab.* 2002; 83(1):100-106.

S. E. Fasoli, H. I. Krebs, and N. Hogan. Robotic Technology and Stroke Rehabilitation: Translating Research into Practice. *Topics in Stroke Rehab.* 2004; 11(4):11-19.

It will be recognized by those skilled in the art that changes or modifications may be made without departing from the broad inventive concepts of the invention. It should therefore be understood that this invention is not limited to the particular embodiments described herein, but is intended to include all changes and modifications that are within the scope and spirit of the invention as set forth in the claims.

The invention claimed is:

1. A system for providing biofeedback corresponding to a gesture of a user, comprising:
   a sensor assembly for detecting muscular activity of a subject and providing sensor signals indicative of the detected muscular activity wherein the sensor assembly comprises a plurality of force sensors spaced apart from one another;
   a processor operable to process the sensor signals, wherein the processor is operable in a set up mode and a therapy mode,
      wherein in the set-up mode the processor is operable to receive the sensor signals from the sensor assembly produced by volitional movements by the subject and calculate a template of predetermined values corresponding to the sensor signals received from the sensor assembly indicative of the muscular activity of the subject during the set-up mode; and
      wherein in the therapy mode the processor is operable to receive the sensor signals from the sensor assembly, compare the sensor signals against the template of predetermined values and provide an output signal based on the variation between the received sensor signals and the predetermined values, wherein the output signal can be used to provide feedback to the user.

2. The system of claim 1 comprising a retainer for holding the force sensors against or adjacent the subject for detecting forces caused by muscle contractions of the subject.

3. The system of claim 1 wherein the force sensors comprise force sensing resistors.

4. The system of claim 1 wherein the system comprises an output element for providing a humanly perceivable cue for commencing the muscular activity wherein the humanly perceivable cue is based on the output signal.

5. The system of claim 1 comprising a feedback element connected with the processor, wherein the feedback element receives the output signal from the processor and provides a human recognizable feedback based on the output signals from the processor.

6. The system of claim 1 wherein the desired movement is movement of a first body part and the sensor assembly is configured so that the force sensors detect the muscular activity of a second body part remote from the first body part.

7. The system of claim 6 wherein comprising a retainer configured to retain the sensor assembly on the second body part.

* * * * *